United States Patent [19]
Gleich et al.

[11] Patent Number: 5,928,883
[45] Date of Patent: Jul. 27, 1999

[54] EOSINOPHIL GRANOLE PROTEINS AS INDICATORS OF INFLAMMATORY BOWEL DISORDERS

[75] Inventors: Gerald J. Gleich, Rochester, Minn.; Aaron M. Levy, San Francisco, Calif.

[73] Assignee: Mayo Foundation for Medical Education, Rochester, Minn.

[21] Appl. No.: 08/968,206

[22] Filed: Nov. 12, 1997

Related U.S. Application Data

[60] Provisional application No. 60/030,548, Nov. 13, 1996.
[51] Int. Cl.$^6$ .......................... C12Q 1/28; C01N 33/573; C01N 33/68
[52] U.S. Cl. ........................ 435/7.21; 435/7.24; 435/7.4; 435/28; 435/963; 436/86; 436/176; 436/540; 436/542
[58] Field of Search ........................... 435/7.21, 28, 963, 435/7.4, 7.24; 436/86, 176, 540, 542

[56] References Cited

U.S. PATENT DOCUMENTS

| | | | |
|---|---|---|---|
| 4,466,973 | 8/1984 | Rennie | 424/267 |
| 4,626,530 | 12/1986 | Schulte | 514/166 |
| 4,748,022 | 5/1988 | Busciglio | 424/195.1 |
| 5,134,166 | 7/1992 | Bernstein | 514/627 |
| 5,250,293 | 10/1993 | Gleich | 424/78.04 |
| 5,498,410 | 3/1996 | Gleich | 424/78.36 |
| 5,510,339 | 4/1996 | Gleich et al. | 514/171 |
| 5,631,267 | 5/1997 | Gleich et al. | 514/312 |

OTHER PUBLICATIONS

Hallgren et al, Amer. Jour. Med., 86, 56–64, 1989.
Levy et al, Gastroenterology, 108, (4 Suppl.), A861, 1995.
"Airways Obstruction—Bronchial Asthma", *Merck Manual*, 14th Edition, R. Berkow (ed.), Merck Sharp and Dohme Research Laboratories, 622–627, (1982).
"Remington's Pharmaceutical Sciences", 17th Ed., A.R. Gennaro et al. (eds.) Philadelphia College of Pharmacy and Science, 1051–1052, (1985).
Ayars, G.H., et al., "Injurious Effect of the Eosinophil Peroxide–Hydrogen Peroxide–Halide System and Major Basic Protein on Human Nasal Epithelium in vitro", *Am. Rev. Resp. Dis.*, 140, 125–131, (1989).
Barnes, P.J., "Asthma as an Axon Reflex", *The Lancet, 1*, 242–244, (Feb. 1, 1986).
Bascom, R., et al., "Major Basic Protein and Eosinophil–Derived Neurotoxin Concentrations in Nasil–Lavage Fluid After Antigen Challenge: Effect of Systemic Corticosteroids and Relationship to Eosinophil Influx", *J. Allergy Clin. Immunol.*, 84, 338–346, (1989).
Butterfield, J.H., et al., "Chapter 8: Anti–Inflammatory Effect of Glucocorticoids on Eosinophils and Neutrophils", *Anti–Inflammatory Steriod Action: Basic and Clinical Aspects,*, Schleimer et al., editors, Academic Press Inc., 151–198, (1980).
Chen, W.Y., et al., "Effects of Inhaled Lidocaine on Exercise–Induced Asthma", *Respiration, vol. 51, No. 2*, 91–97, (1987).
Choudari, C.P., et al., "Gut Lavage Fluid Protein Concentrations: Objective Measures of Disease Activity in Inflammatory Bowel Disease", *Gastroenterology, vol. 140,,* 1064–1071, ( Apr. 1993).
Downes, H., et al., "Lidocaine Aerosols Do Not Prevent Allergic Bronchoconstriction", *Anesth. Analg., vol. 60, No. 1*, 28–32, (1981).
Dunnill, M.S., "The Pathology of Asthma, with Special Reference to Changes in the Bronchial Mucosa", *J. Clin. Path., 13*, 27–33, (1960).
Dvorak, A.M., "Ultrastructural Evidence for Release of Major Basic Protein–Containing Crystalline Cores of Eosinophil Granules in Vivo: Cytotoxic Potential in Crohn's Disease", *The Journal of Immunology, vol. 125, No. 1*, 460–462, (Jul. 1980).
Ellis, A.G., et al., "The Pathological Anatomy of Bronchial Asthma", *J. Med. Sci., 136*, 407–429, (1908).
Enright, P.L., et al., "Effect of Lidocaine on the Ventilatory and Airway Responses to Exercise in Asthmatics", *Am. Rev. Resp. Disease, 122*, 823–828, (1980).
Filley, W.V., et al., "Identification by immunofluorescence of eosinophil Granule major basic protein in lung tissues of patients with bronchial asthma", *The Lancet, 2*, 11–16, (1982).
Frigas, E., et al., "Cytotoxic Effects of the Guinea Pig Eosinophil Major Basic Protein on Tracheal Epithelium", *Lab. Invest., 42*, 35–43, (1980).
Frigas, E., et al., "Elevated Levels of the Eosinophil: Granule Major Basic Protein in the Sputum of Patents with Bronchial Asthma", *Mayo Clinic. Proc. 56:345*, (1981).
Fujisawa, T., et al., "Regulatory Effects of Cytokines on Eosinophil Degranulation", *J. Immunol., 144*, 642–646, (1990).
Gaspari, M.M., et al., "A Method of Obtaining, Processing, and Analyzing Human Intestinal Secretions for Antibody Content", *Journal of Immunology Methods, vol. 109, No. 1*, 85–91, (1988).
Gleich, G.J., "Cytoxic Properties of the Eosinophil Major Basic Protein", *J. Immunol., 123*, 2925–2927, (1979).
Gleich, G.J., "Identification of a Major Basic Protein in Guinea Pig Eosinophil Granules", *J. Exp. Med., 137*, 1459–1471, (1973).
Gleich, G.J., et al., "The Eosinophilic Leukocyte: Structure and Function", *Adv. Immunol., vol. 39*, 177–253, (1986).
Gross, N.J., et al., "Chapter 34: Anticholinergic Drugs", *Allergy, Principles and Practice, vol. 1*, E. Middleton Jr. et al., ed., The C.V. Mosby Company, Publisher, 782–808, (1988).

(List continued on next page.)

*Primary Examiner*—David Saunders
*Attorney, Agent, or Firm*—Schwegman, Lundberg, Woessner & Kluth, P.A.

[57] ABSTRACT

A diagnostic method is provided for inflammatory bowel disorders (IBD), based on the relative levels of eosinophil granule proteins in physiological samples obtained from the GI tract of mammals suspected of having an IBD.

12 Claims, 3 Drawing Sheets

OTHER PUBLICATIONS

Gundel, R.H., et al., "Repeated Antigen Inhalation Results in a Prolonged Airway Eosinophilia and Airway Hyperresponsiveness in Primates", *J. Appl. Physiol.,* 68, 779, (1990).

Hamid, Q., et al., "Expression of mRNA for Interleukin–5 in Mucosal Bronchial Biopsies from Asthma", *J. Clin. Invest.,* 87, 1541, (1991).

Harlin, S.L., et al., "A Clinical and Pathologic Study of Chronic Sinusitis: The Role of the Eosinophil", *J. Allergy Clin. Immunol.,* 81, 867, (1988).

Hastie, A.T., et al., "The Effect of Purified Human Eosinophil Major Basic Protein on Mammalian Ciliary Activity", *Am. Rev. Resp. Dis.,* 135, 845, (1987).

Horn, B.R., et al., "Total Eosinophil Counts in the Management of Bronchial Asthma", *N. Engl. J. Med.,* 292, 1152, (1975).

Krasnowska, M., et al., "A Test of Lidocaine Usage in the Treatment of Bronchial Asthma", *Pneum. Pol.,* 50, 269–273, (1982).

Lamas, A.M., et al., "Glucocorticoids Specifically Decrease Eosinophil Survival", *J. Allergy Clin. Immunol.* 85, Abstract No. 554, 282, (1990).

Lamas, A.M., et al., "Human Endothelial Cells Prolong Eosinophil Survival", *J. Immunol.,* 142, 3978, (1989).

Mauser, P.J., et al., "The Effect of Anti–Il–5 on Antigen-–Induce Airway Hyperreactivity and Pulmonary Eosinophilia in Guinea Pigs", *Am. Rev. Respir. Dis.,* 145, A859, (1992).

Motojima, S., et al., "Toxicity of Eosinophil Cationic Proteins for Guinea Pig Tracheal Epithelium in Vitro", *Am. Rev. Resir. Dis.,* 139, 801, (1989).

Rothenberg, M.E., et al., "Human Eosinophil have Prolonged Survival, Enhanced Functional Properties and Become Hypodense when Exposed to Human Interleukin 3", *J. Clin. Invest.,* 81, 1986, (1988).

Saperov, V.N., "The Treatment of Bronchial Asthma with the Aid of Intra–Arterial Injections of Novocain", *Klin. Med.,* 45, 50–54, (1967).

Schleimer, R.P., et al., "Effects of Glucocorticosteriods on Inflammatory Cells Relevant to Their Therapeutic Applications in Asthma", *Am. Rev. Respir., Dis.,* 141, 559, (1990).

Sedgwich, J.B., et al., "Immediate and Late Airway Response of Allergic Rhinitis Patients to Segmental Antigen Challenge", *Am. Rev. Respir. Dis.,* 144, 1274, (1991).

Sehmi, R., et al., "Interleukin–5 Selectively Enhances the Chemotactics Response of Eosinophils Obtained from Normal but not Eosinophilic Subjects", *Blood,* 79, 2952, (1992).

Silberstein, D.S., et al., "Enhancement of Human Eosinophil Cytoxicity and Leukotriene Synthesis by Biosynthetic (Recombinant) Granulocyte–Macrophage Colony–Stimulating Factor", *J. Immunol.,* 137, 3290, (1986).

Silberstein, D.S., et al., "Hemopoietins for Eosinophils", *Hematol. Oncol. Clin. North Am.,* 3, 511, (1989).

Tai, P., et al., "Deposits of Eosinophil Granule Proteins in Cardiac Tissues of Patients with Eosinophilic Endomyocardial Disease", *The Lancet, vol.* 1, 643–647, (Mar. 21, 1987).

Trocme, S.D., et al., "Conjunctival Deposition of Eosinophil Granule Major Basic Protein in Vernal Keratoconjuncitivitis and Contact Lens–Associated Giant Papillary Conjuctivitis", *Am. J. Ophthamol.,* 108, 57, (1989).

Tullett, W.M., "Effect of Lignocaine, Sodium Cromoglycate, and Ipratropium Bromide in Exercise–Induced Asthma", *Thorax,* 37, 737–740, (1982).

Udell, I.J., et al., "Eosinophil Granule Major Basic and Protein and Charot–Leyden Crystal Protein in Human Tears", *Am. J. Opthamol.,* 92, 824, (1981).

Valerius, T., et al., "Effects of IFN on Human Eosinophils in Comparison with Other Cytokines", *J. Immunol,* 145, 2950, (1990).

Wallen, N., et al., "Glucocorticoids Inhibit Cytokine–Mediated Eosinophil Survival", *J. Immunol.,* 147, 3940, (1991).

Wardlaw, A.J., et al., "Eosinophils and mast cells in bronchoalveolar lavage in subjects with mild asthma", *Am. Rev. Resp. Dis.,* 137, 62–69, (1988).

Wasmoen, T.L., et al., "Biochemical and amino acid sequence analysis of human eosinophil granule major basic protein", *J. of Biol. Chem.,* 263, 12559–12563, (1988).

Weller, P.F., "The Immunobiology of Eosinophils", *The New England Journal of Medicine, vol.* 324, Number 14, 1110–1118, (Apr. 18, 1991).

Willoughby, C.P., et al., "Tissue Eosinophils in Ulcerative Colitis", *Scandinavian Journal of Gastroenterology,* vol. 14, 395–399, (1979).

EOSINOPHIL GRANOLE PROTEINS AS INDICATORS OF INFLAMMATORY BOWEL DISORDERS

CROSS-REFERENCE TO RELATED APPLICATION

The application is a continuation-in-part of U.S. provisional application Ser. No. 60/030,548, filed Nov. 13, 1996, incorporated by reference herein.

This invention was made with the support of grants from the National Institutes of Health, DK 07198 and AI 15231. The Government has certain rights in the invention.

BACKGROUND OF THE INVENTION

Inflammatory bowel disorders or diseases (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis, idiopathic proctocolitis, and infectious colitis. Most hypotheses regarding the pathogenesis of IBD concern the implication of immunologic, infectious, and dietary factors.

6-mercaptopurine (6MP) and its prodrug azathioprine (AZA) have been used in the treatment of inflammatory bowel disease (IBD) for over 25 years. Multiple controlled trials and a recent meta-analysis support the efficacy of 6MP and AZA in Crohn's disease. See, J. M. T. Willoughby et al., *Lancet*, ii 944 (1971); J. L. Rosenberg et al., *Dig. Dis.*, 20, 721 (1975). Several controlled trials support the use of AZA in ulcerative colitis, the most recent by Hawthorne and colleagues, in *Brit. Med. J.*, 305, 20 (1992). However, use of 6MP and AZA has been limited by concerns about their toxicities. Dose-related leukopenia is seen in 2–5% of patients treated long-term with 6MP or AZA for IBD. See, for example, D. H. Present et al., *Am. Int. Med.*, 111, 641 (1989); W. R. Connell et al., *Gut*, 34, 1081 (1993).

Due to the complexity of IBD and the risk of drug-related toxicity, a need exists for methods to quickly and accurately diagnose IBD in patients suspected of having such afflictions.

SUMMARY OF THE INVENTION

The present invention provides a diagnostic method comprising:
  (a) obtaining a physiological sample of material from the gastrointestinal tract of a human suspected of affliction with, or afflicted with, an inflammatory bowel disorder;
  (b) determining the level of at least one eosinophil proinflammatory granule protein in said sample, wherein the level is correlated to the presence or absence of said inflammatory bowel disorder. For example, the elevation of the levels of one or more granule proteins, such as EPO, ECP, or a combination thereof, over the level or levels indicative of a human not afflicted with said inflammatory bowel disorder can be indicative of the presence of inflammatory bowel disorder. The present assay is particularly useful to diagnose Crohn's disease or ulcerative colitis. Preferably, the sample is treated with one or more protease inhibitors prior to step (b).

The following abbreviations will be used: Crohn's disease (CD); ulcerative colitis (UC); inflammatory bowel disease (IBD); eosinophil-derived neurotoxin (EDN); eosinophil cationic protein (ECP); eosinophil peroxidase (EPO); eosinophil major basic protein (MBP); protease inhibitors (PI).

DETAILED DESCRIPTION OF THE INVENTION

Figure 1:
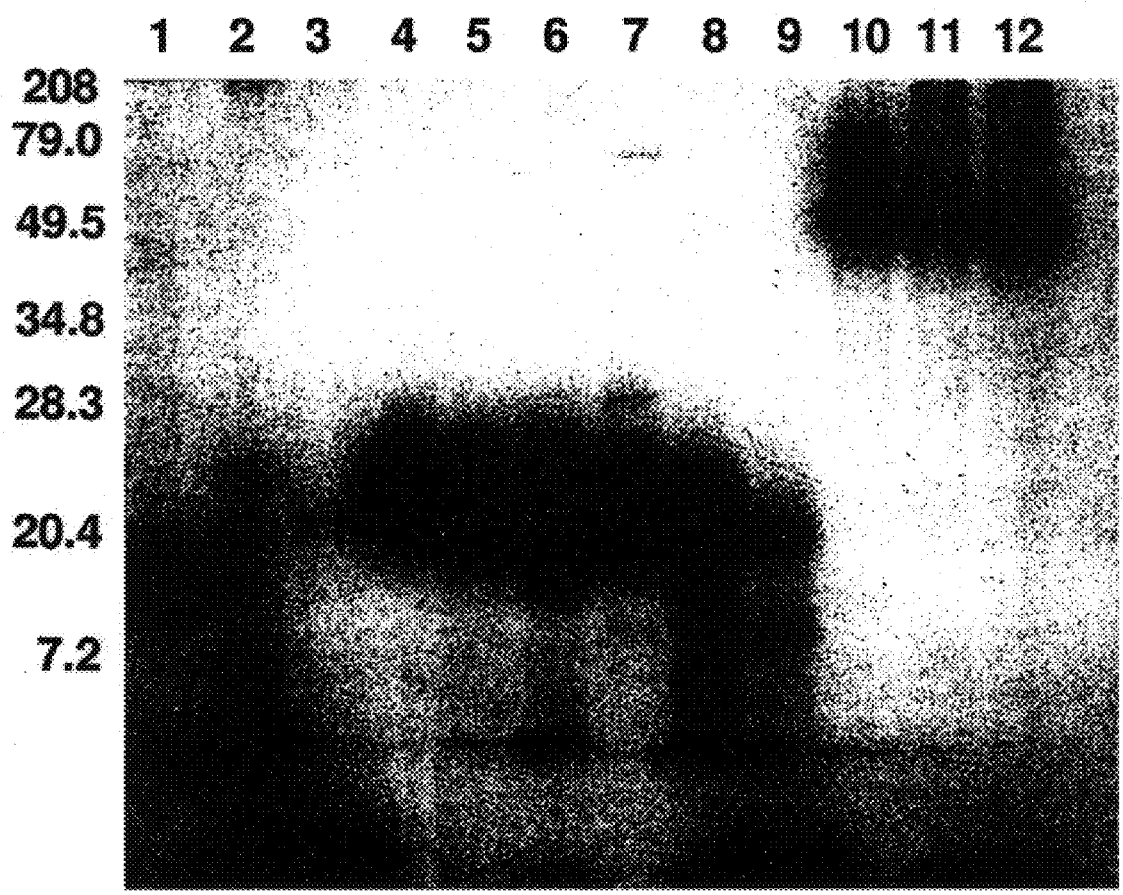
FIG. 1: Autoradiograph of $^{125}$I-labeled eosinophil granule proteins incubated with lavage fluid and PI. Lanes 1–3 are MBP, 4–6 are EDN, 7–9 are ECP, and 10–12 are EPO. Molecular masses of marker proteins are shown on the left in kDa. Protein solutions in lanes 1, 4, 7 and 10 were not preincubated. Protein solutions in lanes 2, 5, 8 and 11 were incubated with gut lavage fluid and with PI for 20 hours at 37° C. Protein solutions in lanes 3, 6, 9 and 12 were incubated with gut lavage fluid, but without PI for 20 hours at 37° C.

Eosinophils are a type of leukocyte containing cytoplasmic granules that stain strongly with acidic dyes. Eosinophils have been associated with bronchial asthma since the early part of this century and they are characteristically found in large numbers in the lung tissue of patients dying of asthma (A. G. Ellis et al., *J. Med. Sci.*, 136, 407 (1908)). In the mid 1970s, it was demonstrated that the severity of bronchial asthma can be related to the number of eosinophils in the peripheral blood of the patients (B. R. Horn et al., *N. Engl. J. Med.*, 292, 1152 (1975)). Also around this time, studies of eosinophils had shown the presence of basic (cationic) granule proteins. The cytoplasmic granules of eosinophils contain four prominent cationic proteins, or "pro-inflammatory granule proteins," namely the major basic protein (MBP), the eosinophil peroxidase (EPO), the eosinophil cationic protein (ECP), and the eosinophil-derived neurotoxin (EDN). These proteins are powerful toxins in vitro and are implicated in the pathophysiology of disease, especially bronchial asthma.

One of the principal proteins associated with eosinophil granules, the major basic protein (MBP), was so named because in the guinea pig it comprises more than 50% of the granule protein, is strongly basic (arginine-rich), and is proteinaceous (G. J. Gleich, *J. Exp. Med.*, 137, 1459 (1973); T. L. Wasmoen et al., *J. Biol. Chem.*, 263, 12559 (1988)). MBP is toxic to worms (helminths) and mammalian cells, and causes damage to bronchial respiratory epithelium (G. J. Gleich et al., *Adv. Immunol.*, 39 177 (1986)). For example, direct application of MBP to respiratory epithelium in concentrations as low as 10 µg/ml ($7.1 \times 10^{-7}$M) causes ciliostasis and epithelial damage. In addition, eosinophils are prominent in the histopathology of Crohn's disease (CD) and chronic ulcerative colitis (UC).

While a pathogenic role for eosinophils and their pro-inflammatory granule proteins has not been established in IBD, histopathological observations document clearly their increased numbers in the mucosa of patients with these diseases (Willoughby et al., *Scand. J. Gastroenterol.*, 14:395–399 (1979); Dvorak, A .M., *J. Immunol.*, 125:460–462 (1980)). A role for eosinophils in the pathogenesis of inflammation at other sites is suggested by correlations between deposition of their inflammatory proteins and tissue injury in the lungs of asthmatics (Filley et al., *Lancet*, 2:11–16) (1982)) and in the endocardium of patients with the idiopathic hypereosinophilic syndrome (Tai et al., *Lancet*, 1:643–647 (1987)). Moreover, the pro-inflammatory effects of eosinophil proteins are considered very important in the pathogenesis of asthma (Weller, P .F., *N. Engl. J. Med.*, 324:1110–1118 (1991)); eosinophil protein levels in the bronchial lavage fluid of patients with asthma are correlated with the degree of bronchial hyperreactivity (Wardlaw et al., *Am. Rev. Resp. Dis.*, 137:62–69 (1988)). A putative role for eosinophils in the inflammatory process of IBD would be bolstered by the presence of eosinophil granule proteins in excreta from the gut.

Whole gut lavage with a polyethylene glycol based electrolyte solution has been used previously to quantify secretion of immunoglobulins and other serum proteins from the gastrointestinal (GI) tract (Gaspari et al., *J. Immunol. Methods*, 110:85–91 (1988); Choudari et al., *Gastroenterology*, 104:1064–1071 (1993)). This approach was used to quantify the content of eosinophil granule proteins in the gut. The present invention involves a comparison of the concentrations of eosinophil granule proteins in whole gut lavage fluid between healthy controls and patients with IBD. The eosinophil granule proteins were recovered in increased concentrations from patients with IBD, supporting a role for eosinophils and their pro-inflammatory proteins in the inflammation of IBD, and providing the basis for the present diagnostic assay.

Although, in the examples hereinbelow, eosinophil granule proteins (EGP) were determined by radioimmunoassay, other types of immunoassays can be employed to determine the relative or absolute amount of eosinophil granule protein(s) in the physiological sample, including those assay methods, formats and kits disclosed in U.S. Pat. No. 5,516,639, incorporated by reference herein, wherein the term "hK2" can be replaced by eosinophil pro-inflammatory granule protein or EGP in the discussion of assay methodologies and kits.

Physiological samples from patients include whole gut lavage, as discussed below, mucus, feces, GI tract tissue, including mucosa and submucosa, jejunal effluent and the like.

The invention will be further described by reference to the following detailed examples, wherein patients undergoing whole gut lavage prior to colonoscopy for known or suspected IBD were recruited. The diagnosis of IBD was established by clinical, endoscopic, radiologic, and histologic criteria. Patients were grouped broadly by the anatomical extent of inflammation and its activity, as assessed clinically, endoscopically and histologically. Clinical details of the patients with IBD are shown in Table 1.

TABLE 1

Clinical Data for Patients with Crohn's Disease (CD) or Ulcerative Colitis (UC)

|  | Number (N) | Pattern of Involvement* | Mean Dur. of IBD (years) | Steroids (yes:no) | IBD Active (yes:no) | Sex (M:F) | Age Range (years) |
| --- | --- | --- | --- | --- | --- | --- | --- |
| CD | 9 | I = 4,IC = 3,C = 2 | 13 | 4:5 | 6/2 | 4:5 | 22–58 |
| UC | 8 | Left = 3,Pan = 5 | 13 | 3:5 | 9/0 | 5:3 | 18–72 |

*I = ileal; IC = ileocolonic; C = colonic Left = Left sided; pan = total UC

Healthy volunteers, ages 18–65, were recruited by advertisement to undergo whole gut lavage. Exclusion criteria for the healthy volunteers included a history of any gastrointestinal illness, use of NSAIDs on a regular basis, the use of any prescription medication, a history of food allergy, and pregnancy. The protocol was approved by the Mayo Clinic Institutional Review Board and all patients and controls gave verbal informed consent.

To collect whole gut lavage fluid, subjects were instructed to drink up to 4 liters of Golytely (Braintree Laboratories, Inc., Braintree, Mass.), 8 ounces every 15 minutes, until the fecal output became clear, and to avoid any other intake during the collection period. Specimens (50 ml minimum) were collected using a toilet insert and container. All subjects collected an early lavage specimen when the stools became loose and a late lavage specimen when the output became clear. Specimens were placed on ice in a styrofoam cooler and processed within 12–18 hours.

Lavage fluids were processed as follows: All specimens were centrifuged at 1500 rpm for 25 minutes and the supernatant passed through a glass filter. The filtrate was then stored at −20° C. until analysis. Visual inspection verified that the early samples contained some stool and that the late specimens were clear. Protease inhibitors were not added to the samples at this point.

EXAMPLE 1

Analysis of the stability of eosinophil granule proteins in intestinal lavage fluid To determine which of the eosinophil granule proteins is the best marker of eosinophil degranulation in the gastrointestinal tract, radiolabeled MBP, EPO, EDN and ECP were incubated with late intestinal lavage fluid. A fresh whole gut lavage fluid (late specimen) from a healthy control subject was placed into two 50 ml tubes and immediately centrifuged at 1900 g for 30 minutes, and the clear supernatant fluid was transferred to clean vials. To a 10 ml portion of one of these supernatant solutions, a protease inhibitor (PI) mixture was added containing the following: 1.0 mg soybean trypsin inhibitor in 1.0 ml of PBS, 0.55 ml of 1.0M EDTA in PBS, 0.23 ml of 100 mM phenylmethylsulfonyl fluoride in 95% ethanol and 0.472 ml calf serum (Sigma Chemical Co., St. Louis, Mo.) (Gaspari et al., *J. Immunol. Methods*, 110:85–91 (1988)). Eosinophil granule proteins were purified, as described earlier (Gleich et al., *J. Clin. Invest.*, 57:633–640 (1976); Gleich et al., *Proc. Natl. Acad. Sci. USA*, 83:3146–3150 (1986); Ten et al., *J. Exp. Med.*, 169:1757–1769 (1989)), and radiolabeled by the chloramine T method, as described previously (McConahey et al., *Int. Arch. Allergy Appl. Immunol.*, 29:185–189 (1966)).

Next, 20 μl of $^{125}$I-labeled eosinophil granule protein at approximately 7 ng/20 μl in PPF-E buffer [0.1% protamine sulfate (Sigma, St. Louis, Mo.), 0.1M phosphate buffer (pH 7.5), 0.5% newborn fetal calf serum (Pel-Freez, Rogers, Ariz.), 0.1% NaN$_3$, and 0.01M EDTA (Sigma, St. Louis, Mo.)], at pH 7.5, was added to 20 μl of the lavage fluid samples both with and without PI and incubated for 20 hours at 37° C. Following incubations, proteins were analyzed by one-dimensional sodium dodecyl sulfate-polyacylamide gel electrophoresis (SDS-PAGE) (Gleich, *Proc. Natl. Acad. Sci. USA*, 83:3146–3150 (1986)), with high range molecular weight markers (Bio-Rad, Hercules, Calif.) and Coomassie blue staining followed by exposing the dried gel to x-ray film to yield an autoradiograph.

In addition, after exposure of radiolabeled eosinophil granule proteins to intestinal lavage fluid, 10–50 μl samples of these mixtures of radiolabeled proteins and intestinal lavage fluid (with and without PI) were mixed with 0.5 ml of bovine serum albumin (Sigma), 0.1 mg/ml, and 0.5 ml 20% trichloroacetic acid (Fisher Scientific), and the mixture incubated on ice for 30 minutes. Samples were centrifuged at 12,000 g for 5 minutes and supernatants were aspirated. The sediments were dissolved in 0.5 ml of 1M sodium hydroxide and counted in a gamma scintillation counter.

Following incubation of radiolabeled eosinophil granule proteins with intestinal lavage fluids, the proteins were analyzed by SDS-PAGE and the results are shown in FIG. 1. Note that MBP was extensively digested even in the presence of PI. Similarly, ECP was extensively digested by the intestinal lavage fluid, although here the presence of PI markedly diminished ECP degradation. In contrast, both EDN and EPO were remarkably resistant to degradation by intestinal lavage fluid enzymes, even in the absence of PI.

Table 2 shows the results of trichloroacetic acid precipitation of radiolabeled proteins after incubation with intestinal lavage fluid in the presence and absence of PI.

TABLE 2

Stability of Eosinophil Granule Proteins in Lavage Fluids: Effects of Protease Inhibitors (PI)

| Protein | Percentage Labeled Protein Precipitated with TCA | |
|---|---|---|
| | Without PI (%) | With PI (%) |
| MBP | 27 | 51 |
| ECP | 28 | 83 |
| BPO | 87 | 95 |
| EDN | 96 | 96 |

Duplicate determinations of counts precipitated for each $^{125}$I-eosinophil granule protein when treated with trichloroacetic acid (TCA). Counts were normalized to 100% for protein not exposed to lavage fluids.

These results confirm the findings by autoradiography and show that MBP and ECP in the absence of PI were extensively degraded by enzymes in the intestinal lavage fluid. In contrast, EDN, even in the absence of PI, was only slightly effected by exposure to intestinal lavage fluid and 96% of counts were precipitated by trichloroacetic acid. Therefore, among the eosinophil granule proteins, EDN and EPO appeared to be the best markers of eosinophil degranulation, although all four eosinophil granule proteins were measured in the intestinal lavage fluids.

EXAMPLE 2

Measurement of Eosinophil Granule Proteins

The concentrations of eosinophil granule proteins including MBP, EDN, ECP, and EPO in lavage fluid specimens were determined by radioimmunoassay (Ackerman et al., *J. Immunol.*, 131:2977–2982 (1983); Abu-Ghazaleh et al., *J. Leukoc. Biol.*, 52:611–618 (1992)). Purified proteins were isolated from eosinophil granules obtained from eosinophils of patients with marked peripheral blood eosinophilia and served as standards. Each of these granule protein standards and patient specimens were diluted in PPF-E buffer at pH 7.5.

For the EDN, ECP and EPO double antibody immunoassays, the samples were mixed with specific rabbit antisera followed by radiolabeled protein (0.5 ng/tube), and incubated overnight at 4° C. Burro anti-rabbit IgG and normal rabbit serum were added. The tubes were mixed, incubated at 4° C. for 3 hours, and centrifuged. The supernatant fluid was decanted and radioactivity in the precipitate measured in a gamma counter. The results were expressed as a concentration with the units of ng/ml.

The concentration of MBP was determined by an immunoradiometric assay. Lavage fluid samples were reduced and alkylated as described previously (Maddox et al., *J. Exp. Med.*, 158:1211–1226 (1983); Wassom et al., *J. Clin. Invest.* 67:651–661 (1981)). Pooled sera from patients with the hypereosinophilic syndrome were used as a standard. Immunlon-4 96-well plates (Dynatech Laboratories Inc., Chantilly, Va.) were coated overnight with the capture antibody, J13–6B6 (10 μg/ml in phosphate buffered saline). All incubations were at 22° C. on a shaking platform. Wells were washed with washing solution (0.1M PO$_4$, pH 7.5; Tween 20, 10 ml/l). Unbound sites on the wells were then blocked with PPF-E buffer for 20 minutes. Buffer was removed and 100 μl of standard dilution (hypereosinophilic syndrome pool) or unknown sample was placed in the wells (two dilutions per unknown, each in duplicate). The hypereosinophilic syndrome pool standard curve ranged from 2–256 ng/ml. The standards and samples were incubated overnight. After washing, 100 μl of $^{125}$I-labeled J14-8A2 antibody (50 ng/ml in PPF-E) was placed in the wells and incubated for 4 hours. Wells were washed and counted in a gamma scintillation counter. Internal controls included serum specimens from a normal male subject and a patient with the hypereosinophilic syndrome. Preliminary experiments verified that the lavage fluid did not interfere with the assays. The Wilcoxon Rank-Sum test was used to compare the median concentrations of the eosinophil granule proteins.

Figure 2A:
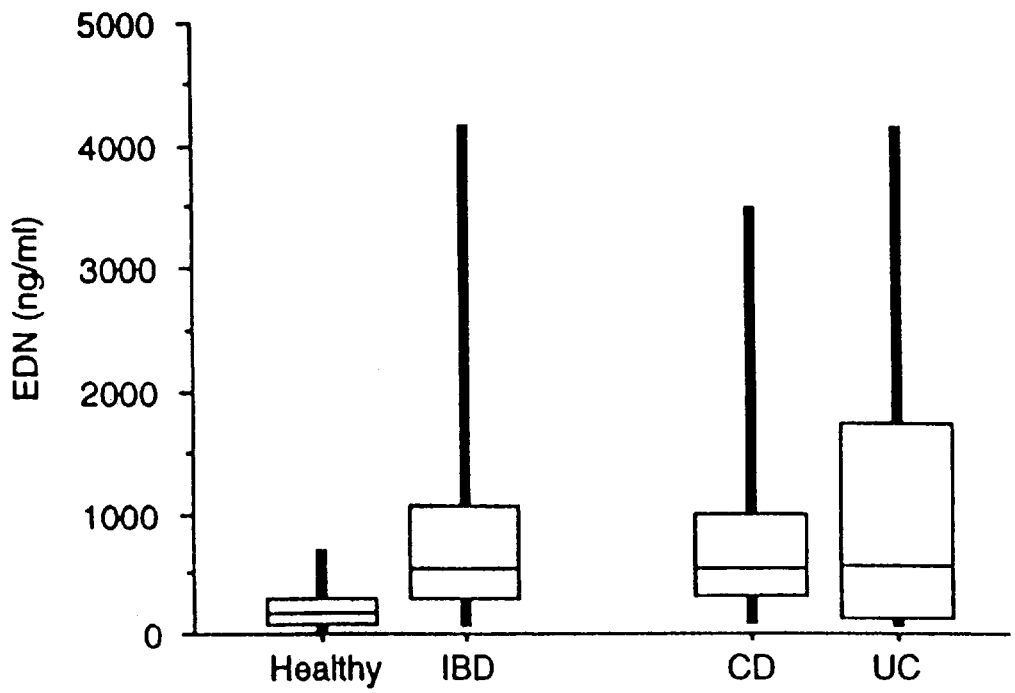
FIG. 2A. EDN (eosinophil-derived neurotoxin) concentrations in early gut lavage fluid. The median EDN concentration was significantly greater in early lavage specimens from IBD patients compared to healthy controls: 538 ng/ml (range 69–4,120) vs. 163 ng/ml (range 13–692), p<0.05 (Wilcoxon Rank Sum). There was no significant difference when Crohn's disease (CD) and ulcerative colitis (UC) were compared. The box encompasses the interquartile range, the vertical bar shows the entire range, and the horizontal line denotes the median.
Figure 2B:
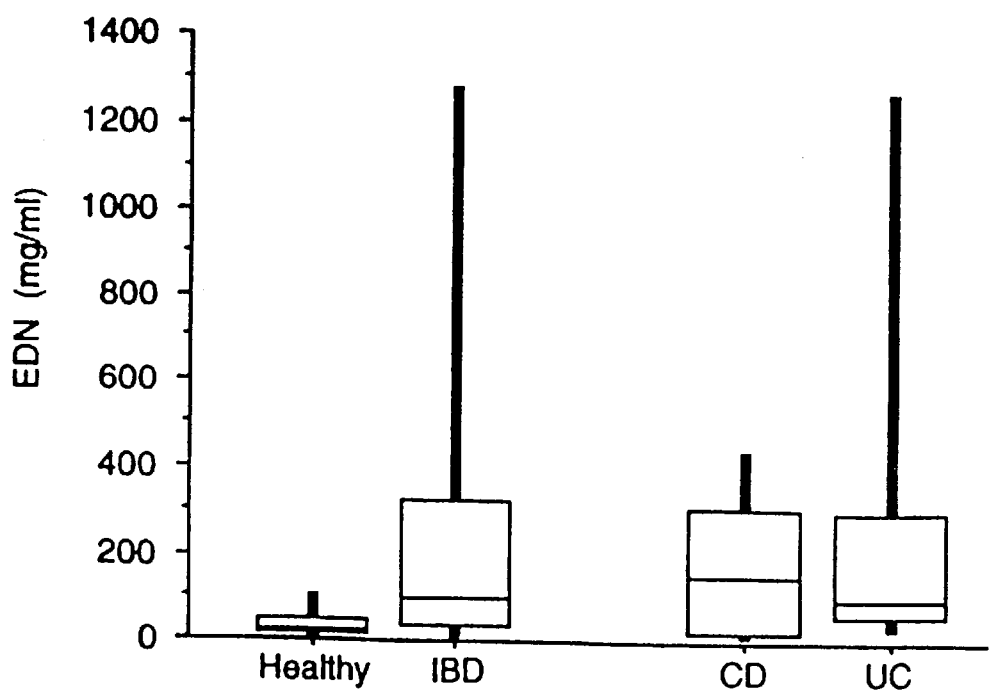
FIG. 2B. EDN (eosinophil-derived neurotoxin) concentrations in late gut lavage fluid. The median EDN concentration was significantly greater in late lavage specimens from IBD patients compared to healthy controls: 282 ng/ml (range 15–1285) vs. 69 ng/ml (range 9–107), p<0.005 (Wilcoxon Rank Sum). There was no significant difference when Crohn's disease (CD) and ulcerative colitis (UC) were compared.

Nine of the 10 healthy controls and all 17 IBD patients completed the protocol. The lavage specimens were immediately placed on ice until the RIA were performed; PI were not added. EDN concentrations in lavage fluids are shown in FIGS. 2A and 2B. Median EDN concentrations were significantly higher in the early and the late specimens from IBD patients than in healthy controls. There were no significant differences in the median EDN concentrations between IBD patients with CD and UC.

Figure 3A:
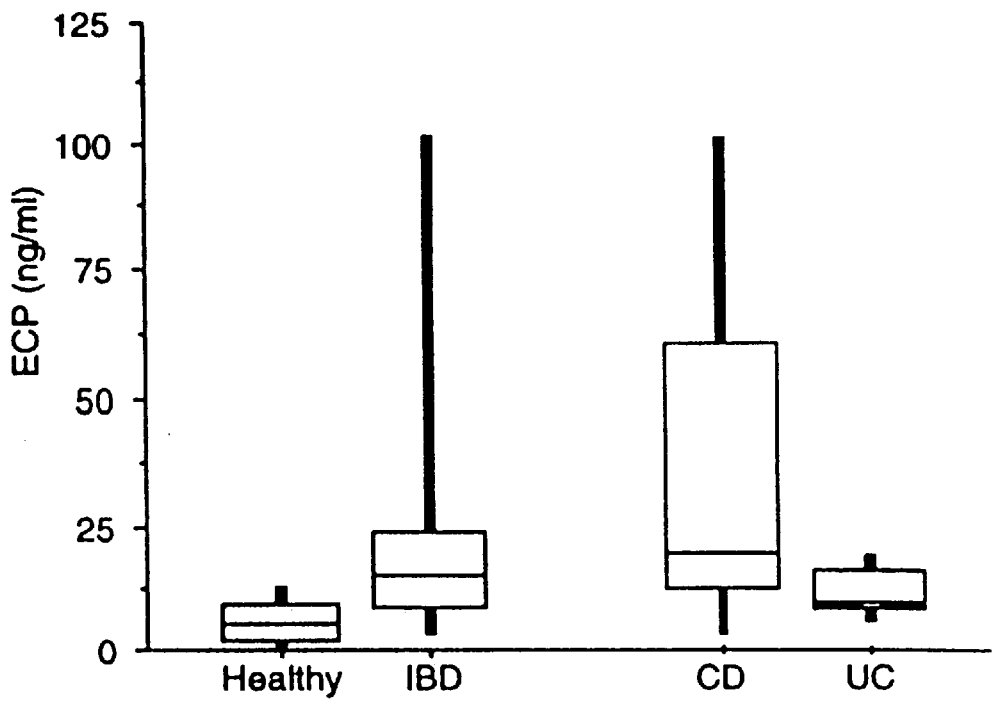
FIG. 3A. ECP (eosinophil cationic protein) concentrations in early gut lavage fluid. The median ECP concentration was significantly greater in early lavage specimens from IBD patients compared to healthy controls: 15 ng/ml (range 3–103) vs. 5 ng/ml (range 1–13), p<0.005 (Wilcoxon Rank Sum). There was no significant difference when Crohn's disease (CD) and ulcerative colitis (UC) were compared.
Figure 3B:
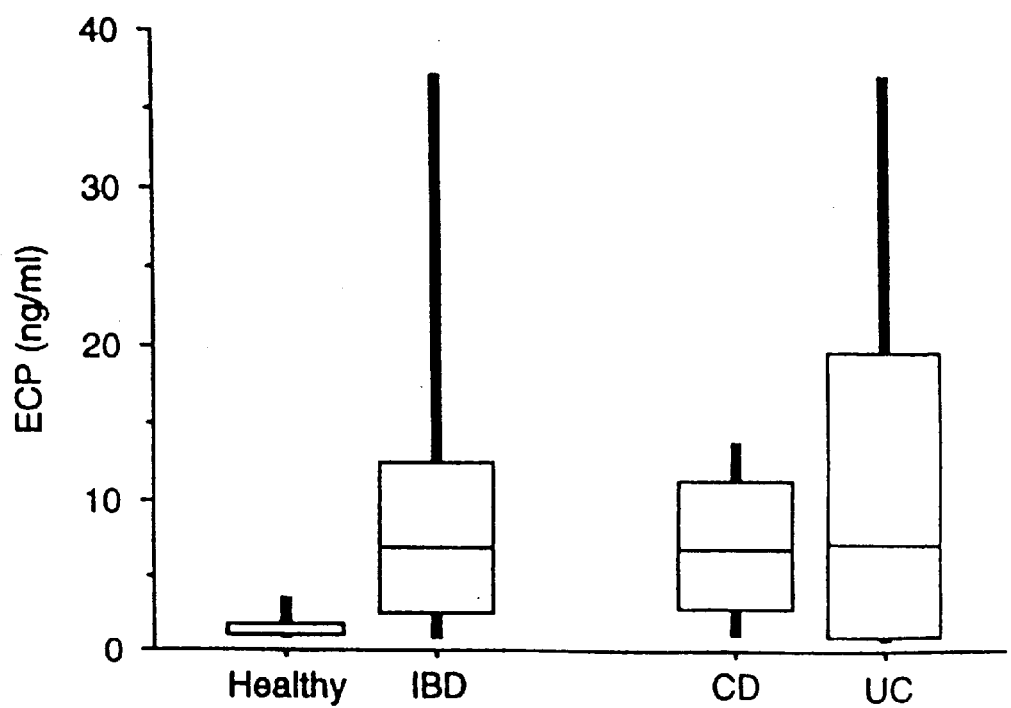
FIG. 3B. ECP (eosinophil cationic protein) concentrations in late gut lavage fluid. The median ECP concentration was significantly greater in late lavage specimens from IBD patients compared to healthy controls: 7 ng/ml (range 1–37) vs. 1 ng/ml (range 1–4), p<0.05 (Wilcoxon Rank Sum). There was no significant difference when Crohn's disease (CD) and ulcerative colitis (UC) were compared.

ECP concentrations in lavage fluids are shown in FIGS. 3A and 3B. Despite the vulnerability to degradation in the absence of PI, ECP concentrations were significantly higher in both early and late specimens from IBD patients compared to healthy controls. Apparently, the rates of proteolysis in lavage fluid were sufficiently inhibited at 0° C. EPO concentrations are shown in Table 3.

TABLE 3

Eosinophil Peroxidase (EPO) Concentrations in Gut Lavage from Patients with Inflammatory Bowel Disease and Controls

| Group | N | EPO (ng/ml) Early Specimen Median | Range | N | EPO (ng/ml) Late Specimen Median | Range |
|---|---|---|---|---|---|---|
| Healthy | 9 | 149 | 11–1512 | 9 | 112 | 11–280 |
| IBD | 17 | 1262* | 154–3821 | 16 | 191† | 29–639 |
| CD | 9 | 1241 | 123–3295 | 8 | 208 | 29–397 |
| UC | 8 | 1162 | 196–1539 | 8 | 159 | 41–639 |

*p < 0.05,
†p = 0.14 (Wilcoxon Rank Sum, compared to healthy controls)

Median EPO concentrations were significantly elevated in the early but not the late specimens from IBD patients, and they were not significantly different between patients with CD and UC. Finally, MBP was not detected in the lavage fluids.

In early specimens, concentrations of the three measurable eosinophil granule proteins were significantly correlated by Spearman rank analysis ($r_s$ for EDN vs ECP=+0.64, p=0.0003, $r_s$ for EDN vs EPO=+0.48, p=0.02; and $r_s$ for ECP vs EPO=+0.68, p=0.0003); in contrast, concentrations of the granule proteins in the late specimens were not correlated. In addition, there were no relationships between the early and late specimens for each granule protein. No clear-cut effects of location, extent or activity of inflammation on the levels of eosinophil granule proteins in lavage fluids were noted.

Discussion

The gut is unique in that, at all anatomic levels, from stomach to rectum, the mucosa normally contains eosinophils (Talley et al., *Gastroenterology*, 103:137–145 (1992)). By contrast, normal skin (Leiferman et al., *Laboratory Investigation*, 62:579–589 (1990)) and respiratory mucosa (Kato M et al., unpublished data) contain few if any eosinophils. On the other hand, in patients with asthma and primates with experimental asthma, the concentrations of eosinophil granule proteins are markedly elevated in bronchoalveolar lavage fluid (Wardlaw et al., *Am. Rev. Respir. Dis.*, 137:62–69 (1988); Gundel et al., *J. Appl. Physiol.*, 68:779–786 (1990)) and are deposited at sites of damage (Filley et al., *Lancet*, 2:11–16 (1982)); these observations support the role of eosinophils in this disorder (Bousquet et al., *N. Engl. J. Med.* 323:1033–1039 (1990)). Further evidence for the eosinophil's importance to the pathogenesis of inflammation in patients with asthma comes from experiments in animal models of this disease in which blocking of eosinophil infiltration (e.g., by antibodies against either eosinophil adhesion molecules or interleukin 5) prevented (Pretolani et al., *J. Exp. Med.*, 180:795–805 (1994); Mauser et al., *Am. Rev. Respir. Dis.*, 148:1623–1627 (1993)), and the administration of eosinophil granule proteins reproduced (Gundel et al., *J. Clin. Invest.*, 87:1470–1473 (1991); Frigas et al., *Lab Invest.*, 42:35–43 (1980)), the physiologic and histologic features of inflammation in asthma.

The eosinophil's constitutive presence in the gut is important because eosinophil granule proteins are pro-inflammatory and damaging to tissues: MBP, ECP and EPO all injure and exfoliate respiratory epithelial cells (Motojima et al., *Am. Rev. Respir. Dis.*, 139:801–805 (1989)), and EDN causes a characteristic syndrome of neurotoxicity when injected intrathecally into guinea pigs (Durack et al., *Proc. Natl. Acad. Sci. USA*, 76:1443–1447 (1979)). In addition, MBP is toxic to mammalian cells including intestinal cells in proportion to dose (Gleich et al., *J. Immunol.*, 123:2925–2927 (1979)), activates complement (Lewis et al., *Immunochemistry*, 13:743–746 (1976)), releases histamine from basophils and mast cells (O'Donnell et al., *J. Exp. Med.*, 157:1981–1991 (1983)), and stimulates superoxide anion and lysozyme release from neutrophils (Moy et al., *J. Immunology*, 145:2626–2632 (1990)). MBP also causes platelets to secrete 5-HT and other bioactive substances in a dose-dependent fashion and affects coagulation by neutralizing heparin, inhibiting Hageman factor, and impairing thrombomodulin (Gleich et al., *J. Exp. Med.*, 140:313–332 (1974); Ratnoff et al., *Am. J. Hematol.*, 42:138–145 (1993); Slungaard et al., *J. Clin. Invest.*, 91:1721–1730 (1993)).

Eosinophils in the lamina propria of the GI tract survive for several days before being shed across the mucosa and the lumen (Teir et al., *Acta Pathol. Microbiol Scand.*, 59:311–324 (1963)). They may also be eliminated from the gut, as they are in other tissues such as the uterus (Ross et al., *J. Exp. Med.*, 124:653–660 (1966)), through engulfment by macrophages, or by undergoing lysis or degranulation followed by degeneration (Kephart et al., *Lab Invest.*, 50:51–61 (1984); Leiferman et al., *N. Engl. J. Med.*, 313:282–285 (1985)). The participation of eosinophils in gastrointestinal inflammation is well known. The clearest example is eosinophilic gastroenteritis in which the degree of tissue injury correlates well with the number of activated, degranulating eosinophils (Keshavarzian et al., *Gastroenterology*, 88:1041–1049 (1985)). Less direct evidence supports a pathogenic role for eosinophil proteins in the inflammation of IBD.

The present examples demonstrate that eosinophil granule proteins are increased in gut lavage fluid from IBD patients, implying that eosinophil degranulation occurs in CD and UC. Validation experiments indicate that EDN is stable in whole gut lavage fluid for at least 20 hours even at room temperature, whereas MBP is degraded even when PI are added to the sample. In addition, we have shown that: 1) EDN, ECP and EPO can be measured in whole gut lavage fluid; 2) the addition of PI is unnecessary for the measurement of EDN and EPO; 3) the medians and ranges of EDN, EPO and ECP concentrations were greater in patients with IBD compared to healthy controls; and 4) the median concentrations of EDN, ECP and EPO were not significantly different between patients with CD and UC.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A diagnostic method comprising:

obtaining a physiological sample of material from the gastrointestinal tract of a human suspected of affliction with, or afflicted with, an inflammatory bowel disorder; and determining the level of the eosinophil pro-inflammatory granule protein eosinophil peroxidase in said sample, wherein the level is correlated to the presence or absence of said inflammatory bowel disorder.

2. The method of claim 1 wherein the elevation of said level of the eosinophil pro-inflammatory granule protein eosinophil peroxidase over a level indicative of a human not afflicted with said inflammatory bowel disorder is indicative of the presence of inflammatory bowel disorder.

3. The method of claim 1 wherein the bowel disorder is Crohn's disease or ulcerative colitis.

4. The method of claim I wherein the sample is obtained by whole gut lavage.

5. The method of claim 1 wherein a protease inhibitor is added to the sample prior to determining the level of the eosinophil pro-inflammatory granule protein eosinophil peroxidase.

6. The method of claim 1 wherein the level is determined by radioimmunoassay.

7. A diagnostic method comprising:

obtaining a physiological sample of material from the gastrointestinal tract of a human suspected of affliction with, or afflicted with, an inflammatory bowel disorder; and determining the level of the eosinophil pro-inflammatory granule proteins eosinophil peroxidase and eosinophil-derived neurotoxin in said sample, wherein the level of the eosinophil pro-inflammatory granule proteins is correlated to the presence or absence of said inflammatory bowel disorder.

8. The method of claim 7 wherein the elevation of said level of said eosinophil pro-inflammatory granule proteins eosinophil peroxidase and eosinophilderived neurotoxin over a level indicative of a human not afflicted with said inflammatory bowel disorder is indicative of the presence of inflammatory bowel disorder.

9. The method of claim 7 wherein the bowel disorder is Crohn's disease or ulcerative colitis.

10. The method of claim 7 wherein the sample is obtained by whole gut lavage.

11. The method of claim 7 wherein a protease inhibitor is added to the sample prior to determining the level of the eosinophil pro-inflammatory granule proteins eosinophil peroxidase and eosinophil-derived neurotoxin.

12. The method of claim 7 wherein the level is determined by radioimmunoassay.

* * * * *

UNITED STATES PATENT AND TRADEMARK OFFICE
CERTIFICATE OF CORRECTION

PATENT NO.: 5,928,883

DATED: Jul. 27, 1999

INVENTOR(S): Gleich et al.

It is certified that errors appear in the above-identified patent and that said Patent is hereby corrected as shown below:

Title page, item [54] and Column 1:
  In the title delete "GRANOLE" and insert --GRANULE--, therefore.
  In column 10, line 18, delete "eosinophilderived" and insert --eosinophil-derived--, therefore.

Signed and Sealed this

Seventeenth Day of October, 2000

Attest:

Q. TODD DICKINSON

*Attesting Officer*      *Director of Patents and Trademarks*